United States Patent
Moskovitz et al.

(10) Patent No.: US 7,625,576 B2
(45) Date of Patent: Dec. 1, 2009

(54) ANTI-BIOCONTAMINANT PRODUCTS AND PROCESSES FOR MAKING THE SAME

(75) Inventors: Mark Moskovitz, Atlanta, GA (US); Chris McDow, Perry, GA (US)

(73) Assignee: Dynamic Adsorbents, Inc., Norcross, GA (US)

( * ) Notice: Subject to any disclaimer, the term of this patent is extended or adjusted under 35 U.S.C. 154(b) by 163 days.

(21) Appl. No.: 11/707,303

(22) Filed: Feb. 15, 2007

(65) Prior Publication Data

US 2008/0118539 A1     May 22, 2008

Related U.S. Application Data

(60) Provisional application No. 60/774,373, filed on Feb. 17, 2006.

(51) Int. Cl.
*A01N 25/04* (2006.01)
(52) U.S. Cl. ............... 424/405; 424/76.8; 424/404; 424/411; 424/421; 424/617; 424/618; 424/630; 424/639; 424/641; 424/650

(58) Field of Classification Search ............... None
See application file for complete search history.

(56) References Cited

U.S. PATENT DOCUMENTS 3,013,897 A    12/1961  Cuprey et al.
5,595,750 A *  1/1997   Jacobson et al. ............ 424/421

OTHER PUBLICATIONS

International Search Report with Written Opinion, dated Sep. 24, 2008, received in international patent application No. PCT/US07/04190, 8 pgs.

* cited by examiner

*Primary Examiner*—Neil Levy
(74) *Attorney, Agent, or Firm*—Holland & Knight LLP; Thomas M. Johnston, Esq.

(57) ABSTRACT

The present invention relates to micro-sized particles having anti-biocontaminant properties. Each particle is comprised of a central metal core, or support structure, (for example, alumina oxide) and has on its surface, one or more anti-biocontaminant metals and at least one redox agent.

20 Claims, 6 Drawing Sheets

ANTI-BIOCONTAMINANT PRODUCTS AND PROCESSES FOR MAKING THE SAME

CROSS REFERENCE TO RELATED APPLICATIONS

This application claims the benefit of U.S. Provisional Application No 60/774,373 filed on Feb. 17, 2006.

TECHNICAL FIELD

The present invention relates to methods and reagents to be used in the deposition of antimicrobial and antiviral substances on porous or non-porous structures or particles. Furthermore, the present invention relates to antimicrobial and antiviral ("antibiocontaminant") products.

BACKGROUND OF THE INVENTION

Microbial infections account for a relatively large portion of U.S. healthcare costs. For example, hospital-acquired microbial infections result in nearly 88,000 deaths each year in the United States, while affecting roughly 2 million people. These infections add an estimated $5 billion to $6.7 billion to healthcare costs annually. See Dresher W H. Copper Helps Control Infection in Healthcare Facilities, Aug. 2004. In view of these numbers, there is a growing interest in efficient methods which produce products having antimicrobial properties; and the products produced therefrom.

An object of the present invention is to provide methods which produce materials and products having the ability to kill microorganisms or inhibit the growth of microorganisms in a wide range of applications.

Gas and liquid filters are frequent sites for the colonization and growth of microorganisms, often leading to changes in the filter's functional characteristics and infection of downstream products. Examples include food and chemical/biotech processing installations, home and institutional water supplies for drinking and other uses, filters for recirculation systems such as vehicle and aircraft cabin air, swimming pools, wash installations and laboratory or high QC manufacture facilities.

Mud baths, for example, are becoming increasingly popular at various resorts and spas across the world. However, while these baths provide for many minerals which may "revitalize" a person's body, they can be a refuge for bacterial growth and colonization.

Dust masks can be susceptible to the capture of growing bacteria and, accordingly, would benefit from the application of antimicrobial and antiviral reagents, for example nanoscale antimicrobial metals, wherein the reagent(s) can penetrate and bind to the semi-porous structure.

Camping equipment, such as straws and canteens, can be vulnerable to the capture and seeding of bacteria and fungi. This equipment would be well-suited for the application of antimicrobial reagents, for example nanoscale antimicrobial metals, wherein the reagent(s) can bind to the structure and serve as a filtering mechanism, guarding the camper against drinking bacteria-laden liquid.

Other materials and products in need of efficient antimicrobial and antiviral characteristics include medical equipment such as mechanical ventilators, hospital linens, water supply systems, catheters and other biodevices.

Many of the existing methods presently used for providing antimicrobial protection to materials are unable to efficiently remove, or inhibit the growth of, microbe(s) because the reagent providing the protection is unable to reach deep into the pores and crevices present in and on the materials and products. A further problem with existing methods is a rapid desorption of the antimicrobial from the material or product, rendering the material ineffective after a short period of time. The converse to this problem is a stable composite that is unreactive and thus ineffective against the removal or inhibition of microbes. Current methods often require multiple steps: pre-treat, drying, mixing, calcining, post-treatment, and final drying. These methods are often time consuming and require large capital expenses.

The present invention ameliorates the foregoing issues by providing methods which can be used to develop antimicrobial and antiviral materials (herein described as "anti-biocontaminants") and products, wherein the materials and products provide a high surface area and/or porous structure for efficient exposure to the antibiocontaminant reagent as used herein.

The present invention allows for one to adjust the stability and reactivity of the antimicrobial agent disclosed herein. This compromise between stability and reactivity is achieved through a two-step mix and dry process. Antibiocontaminant reagents used in conjunction with the present methods are able to penetrate into the porous structure of any material thereby providing a larger area of potential antimicrobial contact as compared to prior art methods. The methods described herein produce materials and products that are adjustable in the quantities of deliverable antimicrobial reagents. The methods described herein produce materials and products having the ability to kill microorganisms and viruses and/or inhibit the growth of microorganisms and viruses in a wide range of applications.

Furthermore, the present invention is directed to anti-biocontaminant products. Another object of the present invention is to provide products having water resistant anti-biocontaminant activity and thus maintains antimicrobial activity in water-contacting environments.

SUMMARY OF THE INVENTION

Figure 1A:
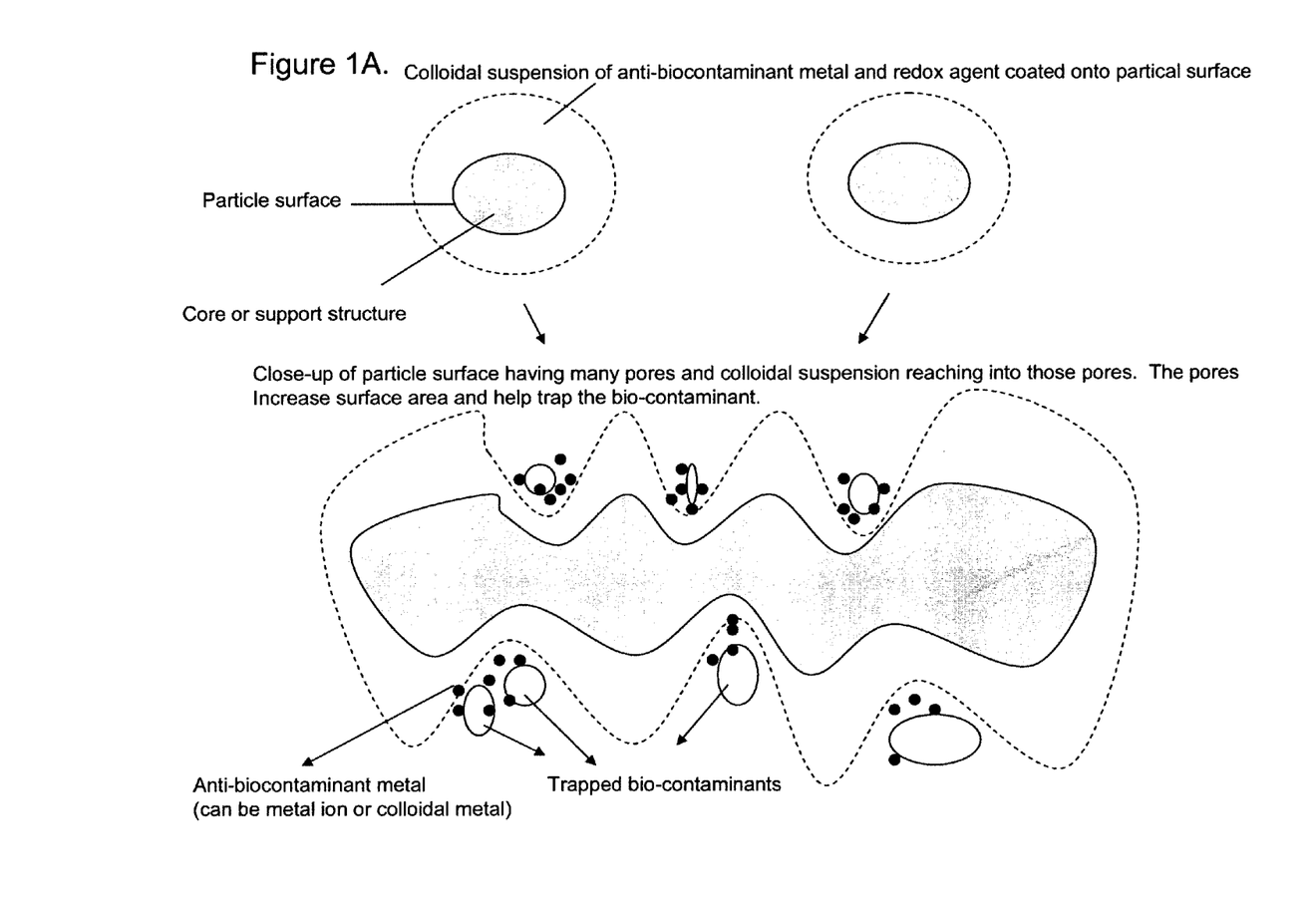
Figure 1B:
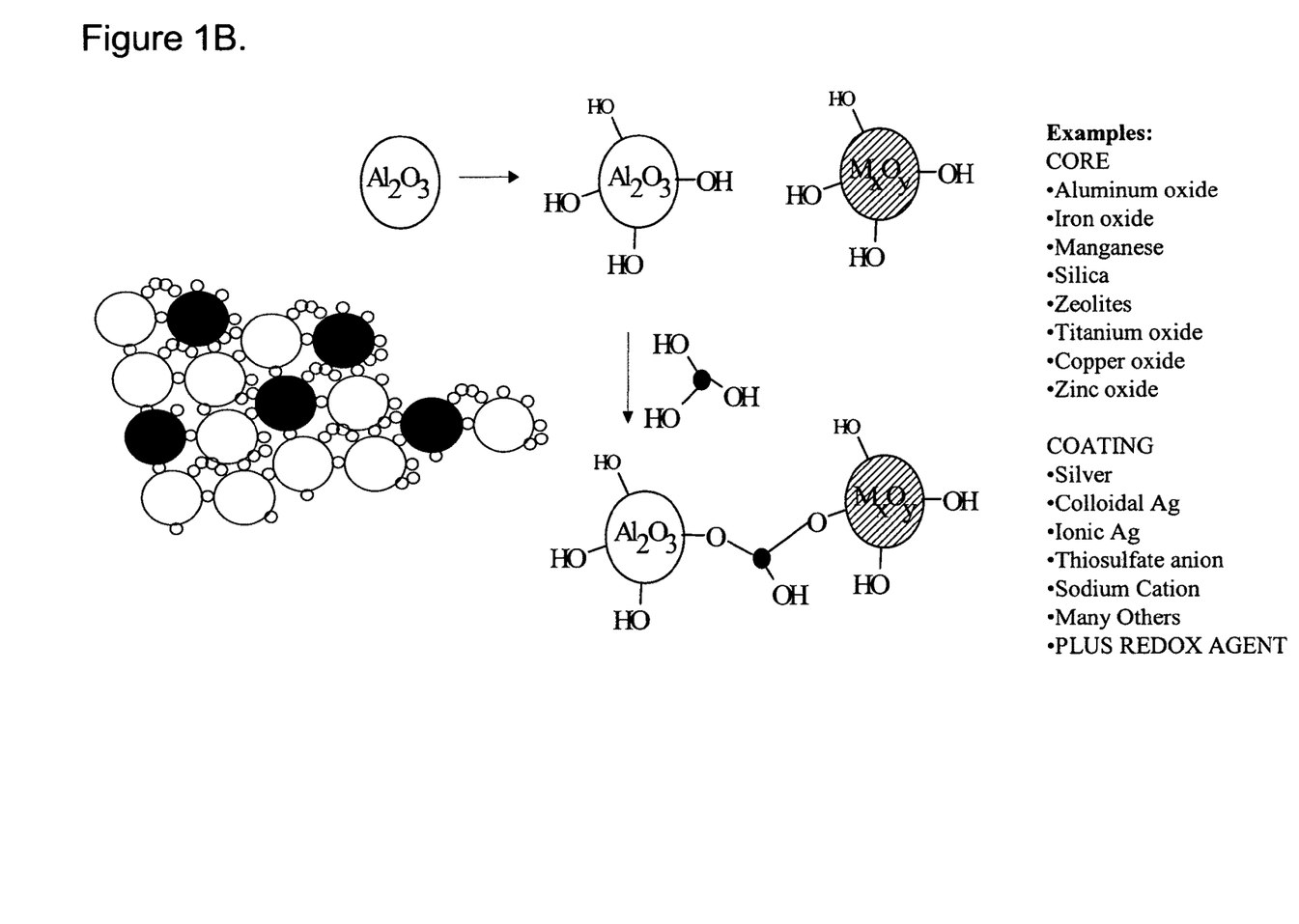

The present invention relates to micro-sized particles having anti-biocontaminant properties. Each particle is comprised of a central metal core, or support structure, (for example, alumina oxide) and has on its surface, one or more anti-biocontaminant metals and at least one redox agent. See FIG. 1. The anti-biocontaminant metals may be ionic or colloidal. The central core may be a metal or a metal oxide. The invention further relates to the absorption and adsorption of these particles onto a variety of support structures, for example porous (inorganic) compounds. For example, a colloidal suspension comprising one or more metals and at least one redox agent is dispersed onto a support structure, for example a porous structure, allowing the absorption and adsorption of the metal, its ions, and the redox agent into pore voids and onto the surface of the structure. The combination creates a mechanism that can be adjusted for precise functioning by manipulating bed depth (for example, bed depth of a chromatography column), particle size, pore size of the central core, pore size of the coated central metal core, metal loading, moisture and redox agents. The invention has the ability to destroy or inhibit microorganisms in a wider range of applications and with greater efficiency than with the colloidal metal or porous structure alone. The colloidal and/or ionic metal, for example silver, penetrates the pores of the support structure. The formed anti-biocontaminant bead can then be applied to a material to be protected, thereby inhibiting the formation of micro-colony bacterial growth and/or killing the microorganisms already present. The present invention provides a controllable ion release via controlled redox reactions at the surface of the anti-biocontaminant particle. The application of the colloidal metal and redox agent to the surface of the central structure, for example a porous structure, creates an environment where the particle is similar to a microscopic thin layer chromatographic plate or surface. Application of the colloidal metal, or ionic metal, to the surface of the support structure, in combination with the adsorptive properties of the structure, result in an anti-biocontaminant particle having on its surface: metal (colloidal or ionic), one or more redox agents, and metal complexed with the one or more redox agents. If the support structure is porous, the applied colloidal or ionic metal is retained within these pores.

Examples of anti-biocontaminant metals for applying, or dispersing onto, to the surface of the support structure include, but are not limited to, silver, copper, manganese, nickel, tin, zinc, and brass. In one embodiment, one or more of these metals are ionic. In another embodiment, one or more of these metals are colloidal. In yet another embodiment, one or more of these metals are metallic. Such metals may used in a colloidal suspension comprising at least one redox agent for application, or dispersion, onto the target. Silver is a safe metal because, in its metallic state, there is very little that is absorbed into the body. Thus, silver is used as tableware and in artificial teeth. In an ionic state, it exhibits antimicrobial activity. Copper has been used in cotton fibers, latex, and other polymeric materials. Copper technology has produced antiviral gloves and filters, self-sterilizing fabrics like hospital bed linens that kill antibiotic-resistant bacteria, antifungal socks, and anti-dust mite mattresses and mattress covers. See, for example, Borkow and Gabbay, Putting Copper into Action: Copper-Impregnated Products with Potent Biocidal Activities, FASEB J. 2004; 18:1728-1730.

Examples of the central metal core, or support structure, include, but are not limited to: Aluminum oxide, Iron oxide, Manganese oxide, Silica, Zeolites, Titanium oxide, Copper oxide, Zinc oxide, and any of the foregoing metals impregnated with silica gel.

Examples of target materials and products for application of the anti-biocontaminant beads of the present invention include, but are not limited to, alumina, silica, woven and non-woven products, plastic, synthetic fibers, natural fibers, thermoplastic polymers, paper, cloth, mud bath products and minerals, medical wipes, catheters, leather, dust masks, sipping straws, filters, canteens, metal, titanium oxide, zirconium oxide, zeolite, and silica gel. Alumina is an example of a porous structure that is known to have a high surface area to weight ratio due to the pores and tunnels that exist in a given alumina crystal. Examples of thermoplastic polymers include, but are not limited to, polyamides, polyvinyl, polyolefins, polyurethanes, polyethylene terephthalate, and styrene-butadiene rubbers. The anti-biocontaminant beads of the present invention may also be crushed into a fine powder for application to various cloths and dust masks, for example.

FIGURE DESCRIPTIONS

FIG. 1A—Diagrammatic representation of the colloidal suspension-coated beads of the present invention. The core/support structure of each bead may have pores which (1) increase the surface area exposed to the bio-contaminant and (2) trap the biocontaminant.

FIG. 1B—Diagrammatic representation of the core/support beads comprising hydroxyl groups. The hydroxyl groups serve to aid in the formation of complexes of the anti-biocontaminant beads of the present invention.

FIG. 2—Percent reduction in bio-contaminant colony growth.

FIG. 3—Colony growth after 15 seconds contact with colloidal suspension-coated beads.

FIG. 4—Beads prior to coating with colloidal suspension.

FIG. 5—Colloidal suspension coated beads.

DETAILED DESCRIPTION OF THE INVENTION

The ability of a metal to inhibit microorganism growth, or alternatively kill microorganisms, requires direct contact for the reaction to take place. It has been suggested that the presence of colloidal silver near a virus, fungi, bacterium, or any other micro-pathogen disables enzymes required for oxygen-metabolism. The herein described process of applying a colloidal suspension of antimicrobial metal, for example silver, and a redox agent to a porous support structure, for example alumina or alumina oxide, allows the target material to better adsorb the silver. The pores of the support structure "trap" or retain the silver. The resultant anti-biocontaminant bead(s) is useful in the destruction of a variety of micro-pathogens, including viruses. The herein disclosed methods create greater effectiveness and increase the range of applications by taking advantage of the properties of the silver, for example, which are contained in a colloidal mixture. The alumina, for example a porous alumina, provides the surface area necessary to retain the anti-biocontaminant metal and increases the likelihood that an organism will come into contact with the silver. Given the right conditions the silver can desorb and move freely within a complex of beads, or within the material to which the beads are applied. Hydroxyl groups, which emanate from each core support structure, allow for individual beads to complex. See FIG. 1B. The desorption of silver creates further possibilities for the microorganism to come into contact with silver. The greater surface area creates more opportunities for the microorganism to come into contact with the antimicrobial metal, the greater the likelihood the microorganism will be destroyed.

When placed into a packed bed target material, for example material packed into a chromatography column, the tortuous path that is created for the microbial contaminant increases the likelihood that the microorganism will come into contact with a metal adsorbed to the support structure. Fluid velocity that provides turbulent flow through the packed bed increases the likelihood that the microorganism will come into contact with the adsorbed metal. Furthermore, the desorption of a redox agent, for example sodium thiosulfate, interacting with the metal, for example silver, causes an ion release through oxidation and subsequent dissolution of the oxide. In a preferred embodiment, silver cations and the one or more redox agents, complex at the surface of the support structure. This complexation results in the formation of a silver thiosulfate ion complex. These complexes can be further stabilized at the surface of the support structure by the addition of one or more amines. The stabilizing amines may be selected from the group consisting of primary amines, secondary amines, and tertiary amines. An amine is any nitrogen atom comprising at least one substituent. See, for example, U.S. Pat. No. 6,468,521 to Pedersen and U.S. Pat. No. 6,923,990 to Capelli. The anti-biocontaminant beads of the present invention are easily manipulated by adjusting the proportions of ingredients in the colloidal suspension and/or the physical characteristics of the support structure (such as size, pore size, etc.). Such manipulations may be useful when tailoring the structure and function of the beads or powder to the types and/or sizes of bacteria and/or viruses to be inhibited or killed.

DEFINITIONS

"Incipient wetness" refers to the maximum liquid capacity to the point of apparent wetness. It is the maximum amount of liquid that can be contained in a porous solid.

"Colloidal mixture" refers to a mixture where particles are dispersed throughout another substance that cannot be visually detected as separate but can be separated by a semi-permeable membrane. As used herein, the colloidal mixture refers to one or more metals (in ionic, metallic, or colloidal form) and one or more redox agents in a colloidal medium. Alternatively, the foregoing mixture may further comprise one or more amines.

"Colloidal medium" refers to the substance carrying the metals and one or more redox agents. For example the colloidal medium may be water, gelatin, or other polymeric fluids.

"Desorption" refers to the process of removing a sorbed substance by the reverse of adsorption or absorption. For example, the process of removing an adsorbed material from the solid on which it is adsorbed.

"Redox agent" refers to a compound that is involved in a reduction/oxidation reaction.

"Activated" refers to the removal of water in a porous structure revealing adsorbtive sites on the surface of the target material. For example, activated alumina refers to alumina that has been heated to about 250° C. for about 1 hour. An adsorbent has the capacity or tendency to adsorb or cause to accumulate on a surface.

"Methyl Violet" refers to tetramethyl, pentamethyl, or hexamethyl pararosaniline or any combination thereof.

"Methyl Orange" refers to p-dimethylamino-azobenzene-sulfonic acid.

As used herein, the anti-biocontaminant particle "core" is used interchangeably with "support structure."

"Beads" refer to spherical core particles having been coated with a colloidal suspension of the present invention ranging in size from about 100 μm to about 6 mm.

"Powder" refers to core particles, having been coated with a colloidal suspension of the present invention, of any shape less than about 100 μm.

"Biocontaminant" refers to any virus or bacteria to be killed by the present invention.

"Providing an anti-biocontaminant effect to a target material" refers to imparting an anti-microbial or anti-viral activity to the target material via the application of the anti-biocontaminant compositions of the present invention to the target material.

In one aspect of the present invention, a colloidal metal solution is provided and contains between approximately 1% and approximately 4% metal by mass. It is preferred that the colloidal metal solution contain less than 4% metal by mass. It is further preferred that the colloidal metal solution contain less than 3% metal by mass. It is still further preferred that the colloidal metal solution contain less than 2% metal by mass. It is preferred that the colloidal medium is water and 0%-5% gelatin and 0%-5% polymeric fluid. The colloidal mixture of the present invention comprises, for example, at least one redox agent and one or more metals. Redox agents are well known in the art. An example of a redox agent is sodium thiosulfate. The porous (for example an inorganic material, metal oxide, or fibrous material) material can have a surface area between zero and infinity ("∞").

The central support structure may be porous; for example, having a pore diameter of between about 0.1 nm (1 Å) and 50 nm (500 Å). In one embodiment the central structure has a pore diameter of between about 2 nm (20 Å) and 50 nm (500 Å). In yet another embodiment, the central structure has a pore diameter of between 2 nm and 20 nm. The presently described anti-biocontaminant beads may have porous central support structures, wherein the pore size is easily manipulated to accommodate the size of the biocontaminant to be killed. For example, the influenza virus is much smaller than the smallpox virus. It may be necessary to adjust the pore size of the central support structure of each bead to insure that the smaller virus is trapped, or adsorbed, within the pore. Too large of a pore will allow smaller biocontaminants to escape being trapped. The addition of colloidal metal to a porous compound should be between 25% by mass to the incipient wetness point.

Examples of antimicrobial metals include, but are not limited to, silver, copper, any zeolite, manganese, nickel, tin, zinc, and brass. These metals are applied to the surface of each support structure in a colloidal mixture. Silver is a safe metal because, in its metallic state, there is very little that is absorbed into the body. Thus, silver is used as tableware and in artificial teeth. In an ionic state, it exhibits antimicrobial activity. Copper has been used in cotton fibers, latex, and other polymeric materials. Copper technology has produced antiviral gloves and filters, self-sterilizing fabrics like hospital bed linens that kill antibiotic-resistant bacteria, antifungal socks, and anti-dust mite mattresses and mattress covers. See, for example, Borkow and Gabbay, Putting Copper into Action: Copper-Impregnated Products with Potent Biocidal Activities, FASEB J. 2004; 18:1728-1730.

Examples of target materials and products for application of the anti-biocontaminant beads or powder of the present invention include, but are not limited to, woven and non-woven products, plastic, synthetic fibers, natural fibers, thermoplastic polymers, paper, cloth, mud bath products and minerals, medical wipes, catheters, leather, dust masks, sipping straws, filters, canteens, and metal. Alumina is an example of a porous structure that is known to have a high surface area to weight ratio due to the pores and tunnels that exist in a given alumina crystal. Examples of thermoplastic polymers include, but are not limited to, polyamides, polyvinyl, polyolefins, polyurethanes, polyethylene terephthalate, and styrene-butadiene rubbers.

The anti-biocontaminant beads of the present invention can be added or applied to the target materials by methods well known in the art. Such methods include, but are not limited to, spin coating, dip coating, die coating, chemical vapor deposition, incipient wetness, and curtain coating. Alternatively, the beads of the present invention may be applied to a target material by impregnating methods well known in the art. Such methods include, but are not limited to, vacuum impregnation and low temperature impregnation.

The present invention can be effective at the point of incipient wetness or can be dried to low moisture. Application will dictate the moisture content of the invention. Liquid applications requiring a quick leach of metal would prefer the wet embodiment of the invention, wherein leaching refers to the removal of soluble or insoluble constituents by the action of a percolating liquid (i.e. the introduction of a substance into a liquid stream from a stationary solid through mass transfer). Gaseous applications would prefer a drier embodiment of the invention, wherein there is relatively low moisture, for example 0% moisture. Depending on the application, the material can be tailored to maximize the effectiveness. The compound should be dried at 150° C. (above boiling water temp) with a reasonable flow of clean dry air to facilitate the removal of moisture from the system.

Aluminas are multifunctional materials with ratios of active sites and pores. Engineering the active alumina to contain advantageous surface functionalities while reducing undesirable sites is fast becoming a science and is a powerful tool in the design of selective adsorption units. The material has physio-chemical properties.

Having now generally described the invention, the same will be more readily understood through reference to the following Examples which are provided by way of illustration, and are not intended to be limiting of the present invention.

EXAMPLE 1

Alumina Bead Preparation and Test

A 4% silver colloidal solution is prepared by adding 2.78 g silver nitrate, 1.07 g silver fluoride, 1.76 g silver chloride, 1.0 g gelatin, and 970 mg of sodium thiosulfate to enough water to make 100 mLs of solution (Solution A). 33 ml of distilled water was added to 67 ml of solution A (forming Solution B). Solution B was added to 100 g Versal GH (powder), an alumina gel, or pseudoboehmite alumina, gamma alumina, chi-rho alumina, or eta alumina, and/or bayerite alumina. Each of Versal GH, alumina gel, or pseudoboehmite alumina, gamma alumina, chi-rho alumina, or eta alumina, and/or bayerite alumina serve as the central support structure of the subsequently formed anti-biocontaminant beads. The mixture was then dried in a convection oven ramped at 3° C./min to 150° C. and held at 150° C. for 1 hour or until thoroughly dried.

*Staphylococcus aureus* colonies were reduced by an average of 99% and 97%. *Pseudomonas aeruginosa, Mycobacterium smegmatis, Aspergillus niger, Candida albicans*, and *Bacillus subtilis* were also tested.

Approximately 0.18-2.0 grams the test sample (the above-described beads) were weighed and placed into a sterile test tube (in duplicate). Each set of two tubes were inoculated with ~100 to 200 colony forming units (cfus). The tubes were vortexed and allowed to sit for one minute. After one minute, 2 mL of DI water was added to each tube and each tube was vortexed again. The content of each tube was plated in a 150×15 mm plate. The tubes were rinsed with 2 mL of DI water, vortexed and the content added to the plate with the product and DI water. An additional rinse of 1 ml DI water was performed and the rinsate was added to the same plate. Molten (45° C.) TSA was incorporated into each plate and the plates allowed to incubate.

Positive controls were performed by adding the same inoculum volume to 2 mL of DI water. The rinsing and plating was performed in the same way as the test samples. Inoculum verification plates were performed by plating the inoculum volume in molten TSA. Negative controls were performed for the DI water and the TSA used.

Figure 2:
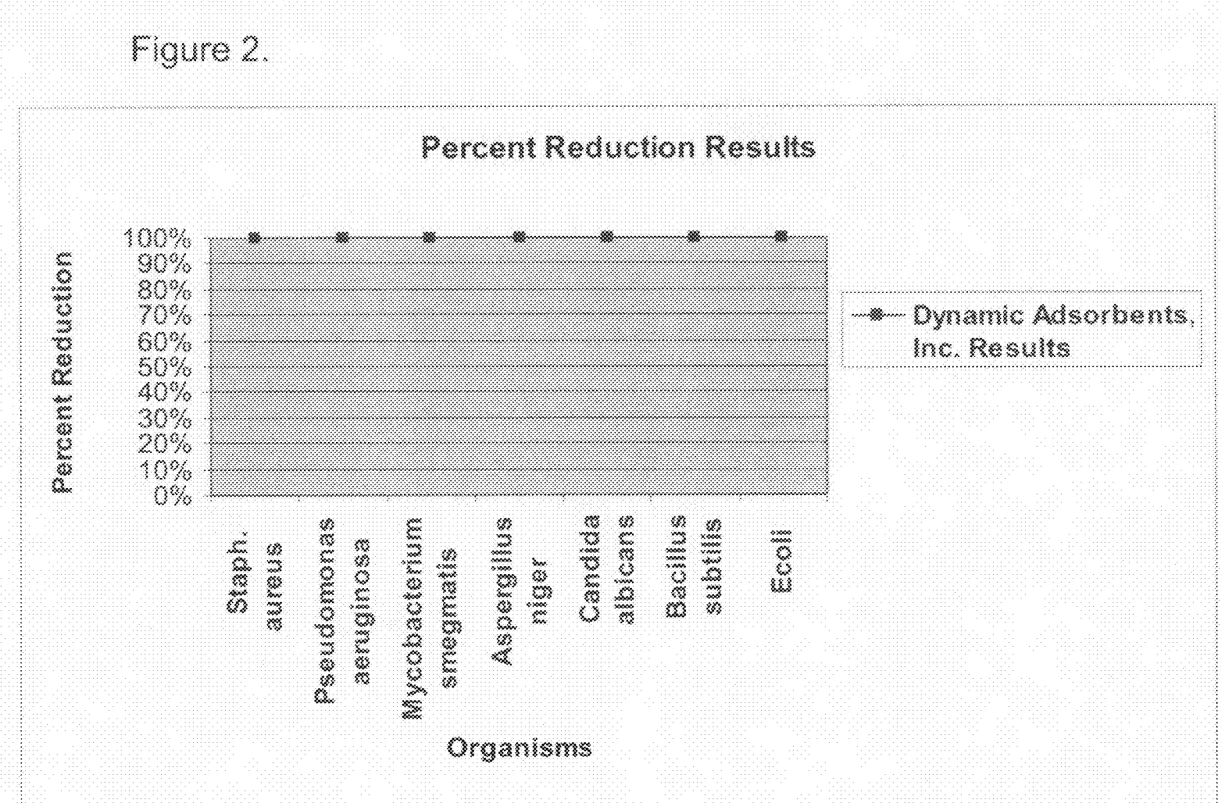

The foregoing protocol resulted in a 98.6% reduction in *Aspergillus niger*; and 98.2% reduction in *Candida albicans*; and 99.2% reduction in *B. subtilis*; 98.6% reduction in *Mycobacterium smegmatis*; a 100% reduction in *Pseudomonas aeruginosa*; a 100% reduction in *Staphylococcus aureus*; and a 100% reduction in *E. coli*. See FIG. 2.

EXAMPLE 2

CFU Recovered after 15 Seconds Exposure to Alumina Beads

Figure 3:
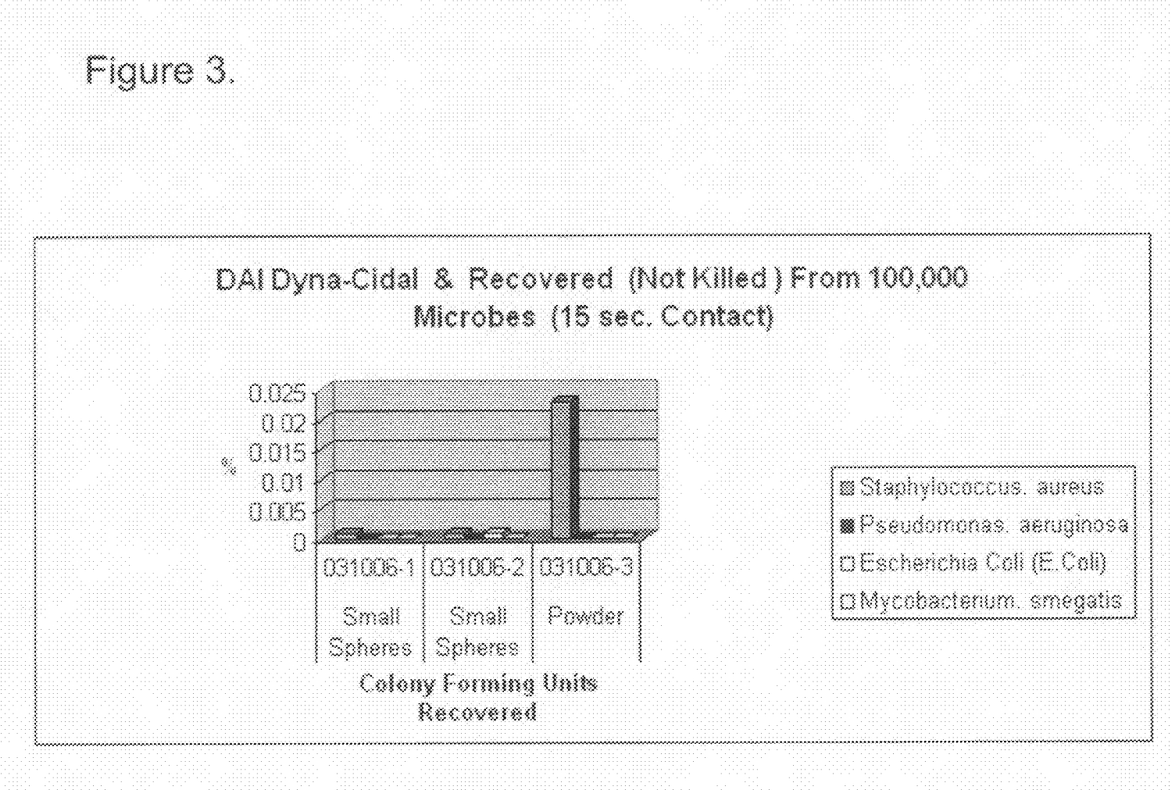
Figure 4:
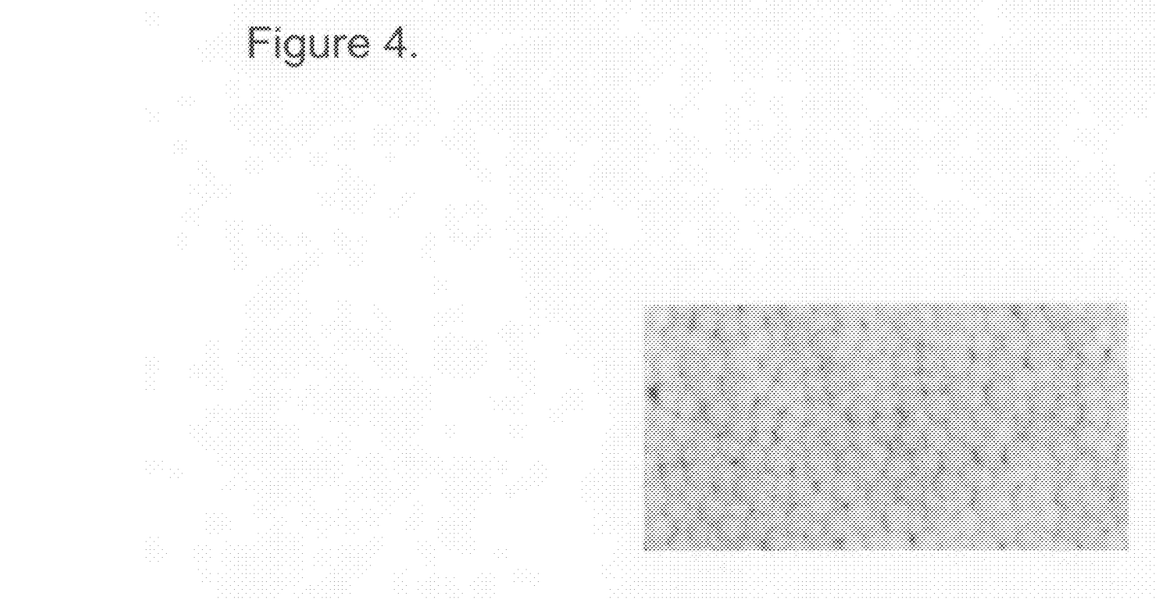
Figure 5:
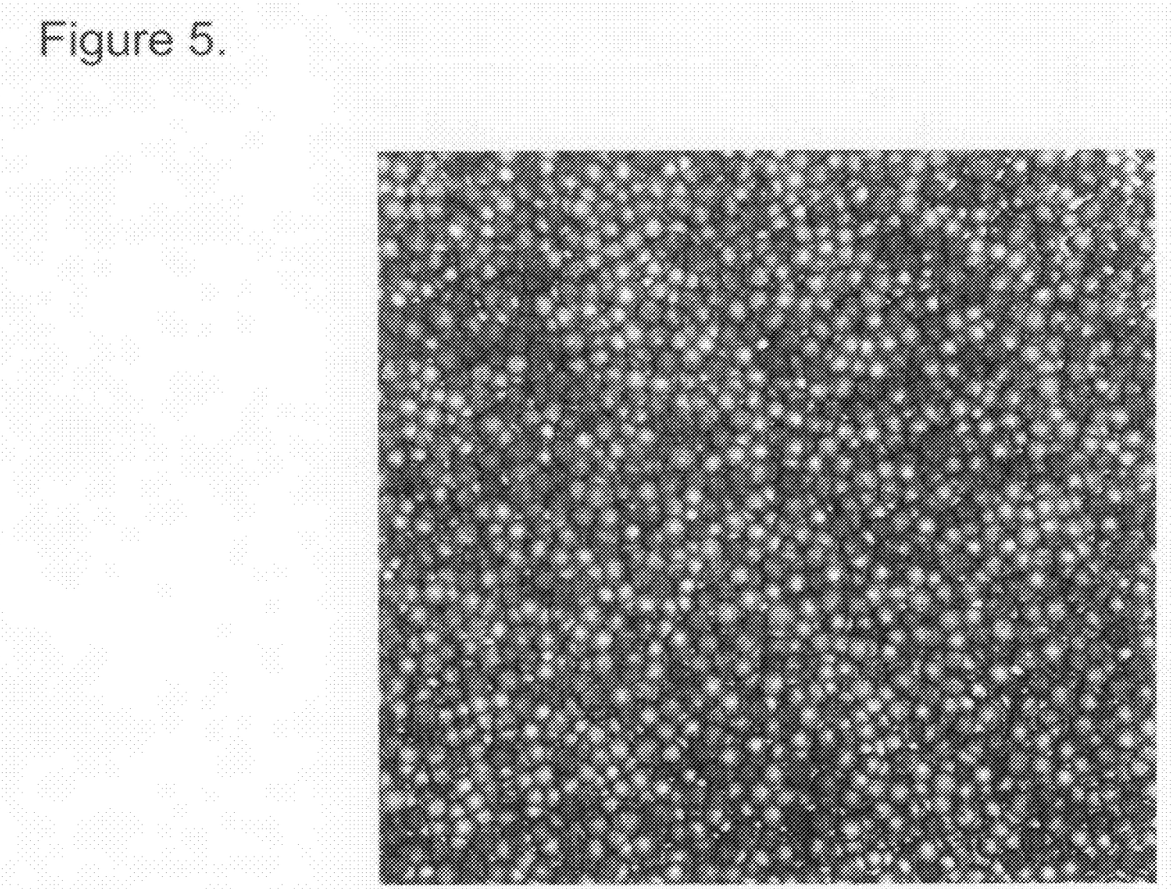

See FIG. 3

| $1.0 \times 10^5$ Bacteria Cells | Small Beads 1 | Small Beads 2 | Powder |
|---|---|---|---|
| *Staphylococcus aureus* | 0.001 | 0.001 | 0.023 |
| *Pseudomonas aeruginosa* | 0 | 0 | 0 |
| *Escherichia coli* | 0 | 0.001 | 0 |
| *Mycobacterium smegatis* | 0 | 0 | 0 |

EXAMPLE 3

TCLP Analysis

Toxic Characteristic Leaching Procedure (TCLP) is an EPA analytical method that simulates leaching in test samples. Based upon concentrations of the TCLP constituents and guidelines set forth in 40 CFR 261.4, the samples can be deemed hazardous or non-hazardous. The samples tested passed the TCLP analysis (the colloidal silver did not leach off of the substrate).

EXAMPLE 4

Kill Time Analysis

Samples were assayed for the time it takes for material to kill a microorganism coming into contact with the sample.

The kill time can be adjusted for each support structure according to the methods described herein. Accordingly, microorganism kill time can be on the order of 2 minutes, 1 minute, 30 seconds, 15 seconds, zero seconds upon contact with the samples described herein.

EXAMPLE 5

Activating Alumina Media for Killing Small Poxyaccinia Virus

Dissolve 20 mg of silver flouride and 14.6 mg of sodium thiosulfate to 850 ml of distilled water and add to 1 kg of activated alumina beads (2 mm to 5 mm in diameter), then add 0.5 g of Methyl Violet and 5 ml of Methyl Orange. Adjust the overall pH to 0.5 by adding acid to the composition. Store overnight. The next day, decant the solution and wash the alumina beads three times with 1 liter of distilled water, decanting the solution after each wash. Further dry the material in an open container for roughly 4 to 5 hours, followed by oven drying at 240° C. to 260° C. for roughly 3 to 4 hours. As an alternative to oven drying, one may dry the alumina beads in a desiccant chamber containing silica gel at roughly 150° C. for about 1 hour. The alumina beads may be impregnated with silica gel. This impregnation enhances the ability to retain various methyl compounds on the surface of the beads.

EXAMPLE 6

Killing Small Pox Using Prepared Alumina Beads or Impregnated Silica Particles from Example 5

Roughly $1 \times 10^5$ to $1 \times 10^6$ cells vaccinia (member of the pox family) viruses were added to silica-gel impregnated alumina beads to approximate 0.5 ml. Roughly 100,000 to 1,000,000 viruses were added to alumina beads, described in Example 5, to approximate 0.5 ml. The viruses and impregnated alumina beads were incubated for 30 minutes at room temperature with moderate shaking. After shaking, the tubes were placed upright and the beads were allowed to settle. The supernatant was then plated onto roughly $1 \times 10^5$ Vero cells. These Vero cells are from a cell line developed from African green monkey nephrocytes. No growth of the virus was observed.

EXAMPLE 7

Percent Reduction of Colony Forming Units Using Alumina Beads or Powder

The procedure followed for the below-identified data was the same as described in Example 1. The "powder" represents granulized alumina beads having been coated, as described in Example 1, with silver and the redox agent, sodium thiosulfate. Such powder is useful for impregnating cloth or face masks, for example.

% CFU Reduction (from 1000 cfus)

| Organism | Alumina Beads1 | Alumina Beads2 | Powder |
|---|---|---|---|
| B. subtilis | 99.9 | 98.5 | 100 |
| E. coli | 100 | 100 | 100 |
| S. aureus | 100 | 100 | 100 |
| P. aeruginosa | 99.4 | 99.8 | 99.5 |
| M. smegatis | 100 | 100 | 99.9 |

EXAMPLE 8

Percent Reduction of Colony Forming Units Using Alumina Beads or Powder

After 15 Seconds Contact Time with Alumina Beads or Powder-Colony Forming Units Recovered

| Organism | Alumina Beads1 | Alumina Beads2 | Powder | Positive inoculum | Inoculum Verified |
|---|---|---|---|---|---|
| S. aureus | 0 | 0 | 0 | 248 | 282 |
| P. aeruginosa | 0 | 0 | 0 | 63 | 43 |
| E. coli | 1 | 1 | 0 | 279 | 272 |
| M. smegatis | 0 | 0 | 0 | 76 | 112 |

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

We claim:

1. A method of providing an anti-biocontaminant effect to a target material comprising:

preparing a colloidal suspension of one or more anti-biocontaminant metals, gelatin, and a redox agent in a colloidal medium;

dispersing the colloidal suspension onto a support structure thereby forming an anti-biocontaminant composition including the support structure, the one or more anti-biocontaminant metals, gelatin, and the redox agent; and applying the anti-biocontaminant composition to the target material.

2. The method of claim 1, further comprising drying the anti-biocontaminant composition prior to applying the composition to the target material.

3. The method of claim 2, wherein the dispersion of the colloidal suspension is a liquid application.

4. The method of claim 1, further comprising drying the target material after applying the anti-biocontaminant composition to the target material.

5. The method of claim 1, wherein the dispersion of the colloidal suspension is a gaseous application.

6. The method of claim 1, wherein the metals are selected from the group consisting of silver, copper, manganese, nickel, tin, zinc, and brass.

7. The method of claim 1, wherein the anti-biocontaminant metals include one or more of ionic metals, colloidal metals, and metallic metals.

8. The method of claim 1, wherein the target material is selected from the group consisting of woven and non-woven products, plastic, synthetic fibers, natural fibers, thermoplastic polymers, paper, cloth, mud bath products, leather, medical wipes, catheters, dust masks, sipping straws, filters, canteens, and metal.

9. The method of claim 1, wherein the anti-biocontaminant composition is applied to the target material by a method selected from the group consisting of spin coating, dip coating, die coating, chemical vapor deposition, curtain coating, incipient wetness impregnation, vacuum impregnation, and low temperature impregnation method.

10. The method of claim 1, wherein the support structure is porous.

11. The method of claim 1, wherein the support structure is non-porous.

12. The method of claim 10, wherein the support structure includes one or more of alumina, alumina gel, pseudoboehmite, gamma, chi-rho, eta, and bayerite alumina.

13. The method of claim 1, wherein the redox agent includes sodium thiosulphate.

14. The method of claim 1, wherein the one or more anti-biocontaminant metals include one or more metal salts.

15. The method of claim 14, wherein the one or more metal salts include one or more of silver nitrate, silver fluoride, and silver chloride.

16. The method of claim 1, wherein the colloidal suspension includes between about 1% to about 4% by mass of the one or more anti-biocontaminant metals.

17. The method of claim 2, wherein drying the composition includes drying the composition at 150° C. for about 1 hour.

18. The method of claim 2, wherein drying the composition includes drying the composition at 150° C. in the presence of a desiccant silica gel.

19. The method of claim 2, wherein drying the composition includes drying the composition at between about 240° C. to about 260° C. for between about 3-4 hours.

20. The method of claim 1, further comprising treating composition with one or more of methyl orange and methyl violet.

* * * * *